US009795131B2

(12) United States Patent
Develter et al.

(10) Patent No.: US 9,795,131 B2
(45) Date of Patent: Oct. 24, 2017

(54) SOPHOROLACTONE COMPOSITIONS AND USES THEREOF

(75) Inventors: Dirk Develter, Maldegem (BE); Mark Renkin, Wiekevorst (BE)

(73) Assignee: ECOVER CO-ORDINATION CENTER N.V., Malle (BE)

( * ) Notice: Subject to any disclaimer, the term of this patent is extended or adjusted under 35 U.S.C. 154(b) by 400 days.

(21) Appl. No.: 14/123,830

(22) PCT Filed: Jun. 6, 2011

(86) PCT No.: PCT/EP2011/059310
§ 371 (c)(1),
(2), (4) Date: Dec. 4, 2013

(87) PCT Pub. No.: WO2012/167815
PCT Pub. Date: Dec. 13, 2012

(65) Prior Publication Data
US 2014/0113818 A1    Apr. 24, 2014

(51) Int. Cl.
*C11D 1/66*     (2006.01)
*A01N 25/30*    (2006.01)
*A01N 43/90*    (2006.01)
*A61K 47/26*    (2006.01)
*A61K 8/60*     (2006.01)
*A61Q 5/00*     (2006.01)
*A61Q 5/02*     (2006.01)
*A61Q 15/00*    (2006.01)
*A01N 49/00*    (2006.01)
*A61Q 19/10*    (2006.01)

(52) U.S. Cl.
CPC ............ *A01N 25/30* (2013.01); *A01N 43/90* (2013.01); *A01N 49/00* (2013.01); *A61K 8/602* (2013.01); *A61K 47/26* (2013.01); *A61Q 5/006* (2013.01); *A61Q 5/02* (2013.01); *A61Q 15/00* (2013.01); *A61Q 19/10* (2013.01); *C11D 1/662* (2013.01); *C11D 1/667* (2013.01)

(58) Field of Classification Search
None
See application file for complete search history.

(56) References Cited

U.S. PATENT DOCUMENTS

| | | | | |
|---|---|---|---|---|
| 5,559,089 A * | 9/1996 | Hartman | ............... | C11D 3/3761 134/42 |
| 5,654,192 A * | 8/1997 | Ducreux | ............. | B09C 1/02 435/101 |
| 6,596,779 B1 | 7/2003 | Jean-Noel et al. | | |
| 7,556,654 B1 * | 7/2009 | Nero | ................ | 8/137 |
| 2004/0120911 A1 * | 6/2004 | Shah | ................ | A61K 8/26 424/70.11 |
| 2004/0171512 A1 * | 9/2004 | Furuta | ................ | C11D 1/662 510/470 |
| 2014/0194336 A1 * | 7/2014 | Develter | ................ | C07H 15/04 510/218 |

FOREIGN PATENT DOCUMENTS

| | | | | |
|---|---|---|---|---|
| CA | 2776029 A1 * | 4/2011 | ............. | A01N 25/30 |
| EP | 0209783 A1 | 1/1987 | | |
| EP | 0209783 B1 * | 6/1990 | ............... | A61Q 9/02 |
| EP | 0499434 A1 | 8/1992 | | |
| EP | 0499434 B1 * | 7/1995 | ......... | C11D 17/0026 |
| EP | 1411111 A1 | 4/2004 | | |
| EP | 1445302 A1 | 8/2004 | | |
| EP | 1953237 A1 | 8/2008 | | |
| FR | 2740779 A1 | 5/1997 | | |
| FR | 2779057 A1 | 12/1999 | | |
| WO | WO 2004/044216 A1 | 5/2004 | | |
| WO | WO 2009/141407 A2 | 11/2009 | | |
| WO | WO 2011/120776 A1 | 10/2011 | | |
| WO | WO 2011/127101 A1 | 10/2011 | | |

OTHER PUBLICATIONS

Hardin et al., Journal of Surgical Research, 2007, 142, 314-319.*
Ashby et al., "The influence of increasing media methanol concentration on sophorolipid biosynthesis from glycerol-based feedstocks", *Biotechnology Letters*, vol. 32(10), pp. 1429-1437 (2010).
Ashby et al., "The use of fatty acid esters to enhance free acid sophorolipid synthesis," *Biotechnology Letters*, vol. 28(4), pp. 253-260 (2006).
Brakemeier A. et al, *Biotechnology letters*, vol. 17, No. 11, Nov. 1995, p. 1183-1188.
Cavalero et al., "The effect of medium composition on the structure and physical state of sophorolipids produced by Candida bombicola ATCC 22214," *Journal of Biotechnology*, vol. 103(1), pp. 31-41 (2003).
Felse et al., "Sophorolipid biosynthesis by Candida bombicola from industrial fatty acid residues," *Enzyme and Microbial Technology*, vol. 40(2), pp. 316-323 (2007).
Fleurackers S. J. J. et al, *Eur. J. Lipid Sci. Technol.* 2010 (112): 655-662.
Fleurackers, "On the use of waste frying oil in the synthesis of sophorolipids," *European Journal of Lipid Science and Technology*, vol. 108(1), pp. 5-12 (2006).
Gorin et al. (*Can. J. Chem.* 1961, vol. 39, 846-855).
Hu et al. "Purification of lactonic sophorolipids by crystallization" *Journal of Biotechnology*, vol. 87, pp. 263-272 (2001).
Van Bogaert et al., "Microbial production and application of sophorolipids," *Applied Microbiology and Biotechnology*, vol. 76, pp. 23-34 (2007).
Van Bogaert et al., "Production of New-to-Nature Sophorolipids by Cultivating the Yeast Candida bombicola on Unconventional Hydrophobic Substrates," *Biotechnology and Bioengineering*, vol. 108(4), pp. 734-741 (Apr. 2011).
Williams, "Biosurfactants for cosmetic application: Overcoming production challenges," *MMG 445 Basic Biotechnology*, vol. 5, pp. 78-83 (2009).

(Continued)

*Primary Examiner* — Abigail Vanhorn
(74) *Attorney, Agent, or Firm* — Knobbe, Martens, Olson & Bear LLP (57) ABSTRACT

The present invention relates to a surfactant composition, consisting of 70 wt %-99.9 wt % sophorolactone, 0-1 wt % sophorolipid acid, less than 0.1% residual substrate, and remainder water. The invention further relates to products comprising this composition or hydrolysates thereof. The invention also relates to uses of these products and hydrolysates.

9 Claims, 4 Drawing Sheets

(56) References Cited

OTHER PUBLICATIONS

International Search Report and Written Opinion of the International Searching Authority for International Application No. PCT/EP2011/059310, mailed on Feb. 17, 2012.
Rau et al., "Sophorolipids: a source for novel compounds," *Industrial Crops and Products,* vol. 13, pp. 85-92 (2001).
Solaiman et al., "Production of sophorolipids by *Candida bombicola* grown on soy molasses as substrate," *Biotechnology Letters,* vol. 26, pp. 1241-1245 (2004).

\* cited by examiner

SOPHOROLACTONE COMPOSITIONS AND USES THEREOF

CROSS-REFERENCE TO RELATED APPLICATIONS

This application is the U.S. National Phase under 35 U.S.C. §371 of International Application PCT/EP2011/059310, filed Jun. 6, 2011.

TECHNICAL FIELD

The present invention relates to compositions comprising sophorolactones of improved stability, to products comprising such compositions, and to uses thereof. In particular, the invention provides highly concentrated sophorolactone compositions of improved purity, both in liquid and solid form. Uses are described where the surface tension lowering capacity, low foaming behavior, stickiness and coating behavior of sophorolactones are beneficial. Compositions of the invention are particularly useful as formulation auxiliaries for industrial and household cleaning products, for pharmaceutical, cosmetic, surface treatments, coatings, agricultural and biocide products, and for wire-drawing formulations, and lubricants.

BACKGROUND

Sophorolipids, formerly known as sophorosides, are glycolipid biosurfactants produced by yeast strains such as *Starmerella (Candida) bombicola, Candida apicola, Candia bogoriensis, Candida batistae* and *Wickerhamilella domercqiae*. They are composed of a disaccharide moiety linked to one hydroxyl group of one w or (w−1)-hydroxy fatty acid that is saturated or monounsaturated. The sugar moiety, i.e. sophorose or 2-O-glucopyranosyl-D-glucopyranose, may further show mono- or diacetylation at the 6' and 6" positions. The nature of the hydroxy fatty acid is characteristic, with the hydroxyl group being located on the n or n−1 carbon atom. The composition of the hydroxylated fatty acid varies depending on the production conditions. Lactonization frequently occurs between the carboxyl group and the 4" OH group of the sophorose, providing sophorolactones in addition to sophorolipids in acid form. Hence, sophorolipids are considered as being a mixture of the compounds presented by the formula I, representing sophorolipids in lactone form, and by formula II, representing sophorolipids in acid form, in which 1. R' and R" represent hydrogen or an acetyl group, or 2. R' is an acetyl group and R"" a hydrogen group, or 3. R' is hydrogen and R" is an acetyl group, or 4. both R' and R" are hydrogen or 5. both R' and R" are acetyl groups. The molecules of formula I are lactonic sophorolipids, also called sophorolactones. The molecules of formula II are open ring sophorolipids, also called sophorolipids in acid form. The carbon chain length n may range from 2 to 17 carbon atoms. Typically the carbon chain length is 16 to 18 carbons long; that is n=13-15.

Sophorolipids are typically produced by fermentation processes wherein a glycolipid producing micro-organism is fed with a sugar supply and a substrate under appropriate fermentation conditions for the production of the sought sophorolipids.

(I)

(II)

The lactone form of sophorolipids has been found to lower surface tension more than does the acid form of sophorolipids. As many applications benefit from a lowering of surface tension and sophorolipids are obtained from renewable resources, sophorolactones are much sought for.

A sophorolactone composition is commercially available from the company Soliance. However, this product comprises relatively high amounts of water and sophorolipids in acid form as well as residual substrate (methyloleate and fatty acids) and is of amber color. This makes the product unsuitable for use in applications that should be substantially free of water and require sophorolactones in concentrated form. Although organic solvents can be used to extract and recover the sophorolactone, this is a highly cumbersome process and thus not economically interesting. Moreover it is often undesirable to have traces of organic solvents in the recovered product.

Unfortunately the currently available production methods provide sophorolactones as part of complex mixtures also comprising sophorolipids in acid form. Although solvents can be used to separate the lactone and acid forms, it is undesirable to have traces of organic solvents and in the end product.

It is known that sophorolactones are sensitive to hydrolysis. Hydrolysis leads to increased formation of the acid form which foams more heavily than the lactone form. It is highly desirable to have sophorolactone compositions which are less prone to hydrolysis, such that their characteristics remain stable and predictable over time.

Therefore there is a demand in the industry for sophorolactone compositions, which are less complex, highly concentrated, easy to formulate, less sensitive to hydrolysis.

It is an object of the present invention to provide concentrated sophorolactone compositions and derivatives with improved surfactant properties, such as hydrolytic stability, foaming behavior, decreased impurity levels, increased ease of handling and formulation. It is also an object of the present invention to provide uses for the sophorolactone compositions and derivatives of the invention.

SUMMARY OF THE INVENTION

The present invention thereto provides a surfactant composition, consisting of 70 wt %-99.9 wt % sophorolactone, 0-1 wt % sophorolipid acid, less than 0.1% residual substrate, and remainder water. By the term "residual substrate" as used herein, is meant substrate residue. Residual amounts of the starting materials that were used as substrate for the micro-organism remain in the end-product. Typical substrate residues are fatty acids or esters such as methyloleate.

By the term residual substrate it is meant herein, a long-chain aliphatic carboxylic acid or ester having the general formula $C_nH_{2n+1}COOH$ or $C_nH_{2n+1}COOR$, wherein n is at least 6, preferably above 8, more preferably above 12, most preferably above 16; and R is an alkyl chain of 1-4 carbon lengths such as a methyl-, ethyl-, propyl-, or butyl- moiety.

The invention further provides a partially hydrolyzed surfactant composition obtained by hydrolyzing the surfactant composition, consisting of 70 wt %-99.9 wt % sophorolactone, 0-1 wt % sophorolipid acid, less than 0.1% residual substrate, and remainder water with 0.5 to 1 equivalents of a base or by heating the sophorolactone for more than 4 hours at a temperature between 70-90° C., preferably to a temperature between 80-90° C., thereby hydrolysing at least part of the sophorolipid lactone to sophorolipid acid and/or its salt.

The invention further provides a formulation comprising the surfactant composition or partially hydrolysed surfactant composition as described above and a solvent with a polarity parameter delta P between 5 and 9.5 and a hydrogen bonding parameter delta H between 8 and 15.

In a preferred embodiment of the formulation of the invention, the solvent is selected from the list of phenoxyethanol, benzyl alcohol, phenetyl alcohol, hydrocinnamylalcohol, dimethylisosorbide, methyl salicylate, 2-3-o-isopropyliden glycerin and eugenol.

In a further aspect, the composition or formulation according to an embodiment of the invention is for the treatment of acne or dandruff. The composition and formulation were found to be effective for the control of acne or dandruff causing organisms. They can advantageously be used for the formulation of composition for the treatment of acne or dandruff.

In a preferred embodiment, the base used for obtaining a partially hydrolysed surfactant as described previously is guanidine or guanidinium hydroxide. Preferably the resulting composition is used for the treatment of allergic reactions, preferably for the denaturation of proteins from arthropods such as dust mites.

In a further aspect uses are provided for the compositions and formulations of the inventions. In a preferred embodiment a composition or formulation according to an embodiment of the invention is used as formulation auxiliary for a household cleaning, industrial cleaning, surface treatment, cosmetic, agrochemical or biocide product, or as template for nanomaterial synthesis.

In another aspect a formulation is provided comprising between 50% and 95% of a composition sophorolactone composition and between 5% to 50% of a non-ionic surfactant, wherein the sophorolactone composition comprises 70 wt %-99.9 wt % sophorolactone, 0-1 wt % sophorolipid acid, less than 0.1% residual substrate, and remainder water.

In a preferred embodiment, the non-ionic surfactant is an alcohol alkoxylate, preferably an alcohol ethoxylate, more preferably an alcohol ethoxylated with a degree of ethoxylation below 8.

In another aspect, uses are provided for the compositions and formulations according to the invention. The concentrated sophorolactone composition of the invention with content of sophorolipids in acid below 1 wt %, expressed in function of the sophorolactone composition, provides access to a number of applications were low-foaming behavior is of importance. In a preferred embodiment the composition or formulation according to an embodiment of the invention is used as formulation auxiliary for a household cleaning, industrial cleaning, cosmetic, and agrochemical or biocide product. The sophorolactone according to an embodiment of the invention in this range of products functions as a formulation aid. It imparts surfactant properties, though does not foam or very little foam is produced. In addition the sophorolactone imparts improved wetting behavior and film-forming properties to the product rendering the treated surface more hydrophilic. This behavior remains present for a limited number of rinsing cycles. Even after repeated rinsing with water the surface treated is more hydrophilic than prior to treatment. The film formation protects co-formulated ingredients from being washed away, removed by sweat, etc. The film-forming properties are advantageous, for instance in anti-fogging formulations or deodorants.

In a preferred embodiment the auxiliary is for a laundry or dishwashing product with a pH of 8.0-14.0, as measured on a 1% solution of the product in water. In a more preferred embodiment the laundry or dishwashing product is in the form of a tablet.

In a preferred embodiment a composition or formulation according to an embodiment of the invention is used as cleaning product for cleaning glass surfaces such as windows.

In a further preferred embodiment, the formulation auxiliary is for improvement of the wetting by water of the surface the product is applied to. Thus antifogging, soil repelling and or the prevention of mineral residue formed upon evaporation of water can be achieved on shower cabinets, windows, mirrors, solar panels, dishware, cutlery and greenhouse foils.

The hydrophobicity and therefore the poor aqueous wettability of plastics often causes moisture to condense as water droplets on the surfaces of plastic films and panels. Condensation of moisture as water droplets obscures visibility due to the poor penetration of light and, in the case of plastics used for food packaging; this causes poor consumer appeal for the products. In situations in which plastic foil or rigid panels are used for enclosures in greenhouses, water condensate reduces the flow of solar light onto the plants. In order to eliminate or minimize the condensation of water as droplets, plastics are very often treated during their manufacture with defogging agents that are blended in during processing, or are treated afterwards.

The most important interfacial property in preventing fogging on plastics is wetting and anchoring to the surface in order to prevent bleeding or being washed away. In case the surfactant was blended in during production it must have the ability to migrate to the surface of the plastic and be oriented in such fashion as to lower the interfacial tension.

In a preferred embodiment a composition or formulation according to an embodiment of the invention is used as a cleaning composition for hard surface cleaning, circuit board cleaning or for cleaning soft metals such as aluminum, lead, tin, copper, zinc or alloys such as terneplate, and wherein the composition has a pH below 7.

In a preferred embodiment, the agrochemical or biocide product is for post-harvest protection of fruit, cereals or vegetables.

In a preferred embodiment, the formulation auxiliary is for improvement of the product's resistance, in particular rain fastness or sweat resistance of the product. This property is advantageous for agricultural applications wherein a pesticide is entrapped in a film or coating left behind by application of the formulation comprising the auxiliary on a plant or soil, or in a cosmetic product such as a deodorant or insect repellant.

In a preferred embodiment, the agrochemical formulation is for seed coating, soil disinfection, slug or snail baiting.

In a further preferred embodiment, the biocide product is for control of lice, mites or other insects.

In a further preferred embodiment, the cosmetic product is a shampoo and the formulation auxiliary is for foam enrichment or foam creaming.

Preferably the composition or formulation according to an embodiment of the invention is used as a wire drawing composition, wherein the composition has a pH below 7.

Preferably the composition or formulation according to an embodiment of the invention is used as a lubricant additive.

In a final aspect of the invention, a method is provided wherein a surfactant composition or a formulation according to an embodiment of the invention, are used for cleaning. In particular, a method is provided for removing oily waste from an object in need of cleaning comprising the steps of:
- providing a surfactant composition or a formulation comprising the surfactant composition according to an embodiment of the invention,
- cleaning the object with the surfactant composition or the formulation thereby generating rinse water comprising sophorolipids and the oily waste, and
- separating the sophorolipids and/or oily waste from the rinse water.

The possibility to recover sophorolipids and/or oily waste from the waste water is advantageous as it allows the reduction of waste. The sophorolipids and/or oily waste can be valorized by use in other applications.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The recitation of numerical ranges by endpoints includes all numbers and fractions subsumed within that range, as well as the recited endpoints.

"Residual substrate" as used herein refers to the non-consumed substrate that was fed during the fermentation as well as its hydrolytic metabolites such as fatty acids.

The present invention provides a surfactant composition, consisting of 70 wt %-99.9 wt % sophorolactone, 0-1 wt % sophorolipid acid, less than 0.1% residual substrate, and remainder water. This composition with decreased acid levels compared to prior art compositions, was found to have an improved hydrolytic stability. This is advantageous as it provides a predictable wetting and foaming behavior. It opens up the use of the composition as auxiliary in a range of products were improved wetting and low foaming are required.

In a preferred embodiment the surfactant composition has a water content below 10 wt %. This makes the composition particularly suitable for use in the manufacturing of products with low solvent content, such as for instance as auxiliary in household products such as dishwashing or laundry tablets.

In a preferred embodiment the auxiliary is for a laundry or dishwashing product with a pH of 8.0-14.0, preferably 8.5-11.50, as measured on a 1% solution of the product in water.

Laundry or dishwashing product in the form of a tablet comprising a surfactant composition according to an embodiment of the invention wherein the surfactant composition consists of 70 wt %-99.9 wt % sophorolactone, preferably at least 95 wt % sophorolactone, more preferably at least 98 wt % sophorolactone, most preferably at least 99 wt % sophorolactone, 0-1 wt % sophorolipid acid, less than 0.1% residual substrate and remainder water.

A method suitable for the production of a sophorolactone composition according to the invention comprises the steps of:
- pre-cultivating cells of a *Candida* species capable of producing sophorolactone, preferably *Candida bombicola* and/or *Candida apicola*,
- cultivating said pre-cultivated cells in an aqueous medium in the presence of at least one fermentable sugar and substrate; the reaction mixture of sugar, substrate and pre-cultivated cells being present in an amount and conditions such that the cells metabolize the sugar and substrate thereby forming sophorolactone and fatty acid,
- suppressing the formation of fatty acid in the reaction mixture below a predetermined level,
- removing the sophorolactone from the remainder of the reaction mixture without adding an organic solvent.

Preferably the sophorolactone is separated from the reaction mixture by crystallization. The sophorolactone crystals can optionally be purified, for instance to decrease the amount of water entrapped in the crystals.

According to the requirements set by an application, the sophorolactone can be transformed into a powder for instance by grinding, or dissolved in a solvent. As sophorolactone has a limited solubility in water and some applications benefit from the absence of water, it is advantageous to provide a sophorolactone composition in liquid form.

The inventor(s) have found that the sophorolactone composition according to an embodiment of the invention can be advantageously combined with a particular selection of solvents. These solvents all have in common that they dissolve sophorolactone particularly well. This is advantageous for providing highly concentrated sophorolactone compositions in liquid form.

The inventors have found a range of solvents that are particularly suitable for dissolving sophorolactones. These solvents have in common that they can be characterized by similar Hansen Solubility Parameters.

Each solvent investigated was given three Hansen parameters, each measured in $(MPa)^{1/2}$: delta D characterizing the energy from dispersion bonds between molecules, delta P characterizing the energy from dipolar intermolecular forces between molecules and delta H characterizing the energy from hydrogen bonds between molecules.

Solvents characterized by a delta P between 5 and 9.5 and a hydrogen bonding parameter between 8 and 15, were found to be particularly suitable as solvent for sophorolactone. Particularly preferred solvents include phenoxyethanol, benzyl alcohol, phenetyl alcohol, hydrocinnamylalcohol, tetrahydrofurfuryl alcohol, dimethylisosorbide, methyl salicylate, eugenol, linalool, hexanol, glacial acetic, dimethylcarbonate, certain glycolethers such as dipropyleneglycol methyl ether and 1-propoxy 2-propanol and lactate esters including ethyl-, butyl-, amyl-, ethylhexyl-lactate.

Preferred solvents according to this invention further include glycerin formal, (2,2-dimethyl-[1,3]dioxolan-4-yl)-methanol known as Solketal and dimethyl lactamide. The respective Hansen solubility parameters of a range of selected solvents and their capability to dissolve sophorolactone are listed in Table 1 and depicted in FIG. 1.

In a more preferred embodiment, the solvent in a formulation according to an embodiment of the invention has a dispersion parameter in excess of 17 $(MPa)^{1/2}$. Such solvents include for example phenoxyethanol, benzylalcohol, phenetyl alcohol, hydrocinnamylalcohol, tetrahydrofurfuryl alcohol, dimethylisosorbide, methyl salicylate and eugenol.

Figure 1:
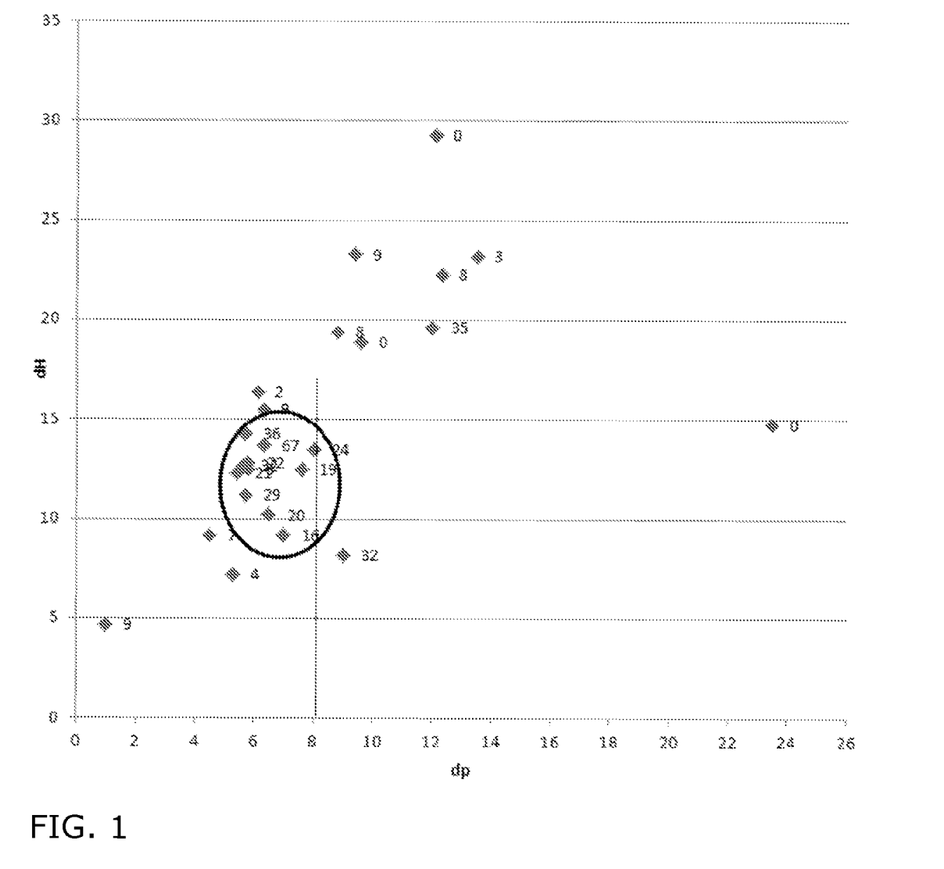
FIG. 1 is a graphic representation of the results of solubility experiments of sophorolactones, expressed in Hansen solubility parameters delta H and delta P.

In FIG. 1, the datapoint numbers representing the percent sophorolactone dissolved at room temperature by the solvents with the particular delta P-delta H combination. The 27 solvents tested in the experiment and depicted in the Figure are as follows: water, glycerol, 1.3 propanediol, propylene glycol, caprylyl glycol, ethanol, phenoxyethanol, benzylalcohol, methanol, isopropanol, phenetyl alcohol, glycerin formal, ethylacetate, DPM, PNP, PNB, ethyllactate, isoamyl lactate, butyl lactate, glacial acetic, D-limonene, hexanol, dimethyl lactamide, DMI, glycerincarbonate, 2-3-o-isopropyliden glycerin, hydrocinnamylalcohol. Of these solvents the following were able to dissolve sophorolactone in excess of 15%: phenoxyethanol, benzylalcohol, phenetyl alcohol, glycerin formal, DPM, PNP, ethyllactate, isoamyl lactate, butyl lactate, dimethyl lactamide, DMI, 2-3-o-isopropyliden glycerin, hydrocinnamylalcohol. And the following solvents were able to dissolve sophorolactone in excess of 30%, the exact amount specified in brackets (also featuring in FIG. 1): phenoxyethanol (36%), benzylalcohol (67%), glycerin formal (35%), dimethyl lactamide (66%), DMI (32%), 2-3-o-isopropyliden glycerin (36%), hydrocinnamylalcohol (33%).

In a further aspect formulations are provided comprising a surfactant composition according to an embodiment of the invention and a solvent with a polarity parameter delta P between 5 and 9.5 and a hydrogen bonding parameter delta H between 8 and 15.

Particularly preferred solvents for dissolving sophorolactone are phenoxyethanol, benzyl alcohol, phenetyl alcohol, hydrocinnamylalcohol, dimethylisosorbide, methyl salicylate, 2-3-o-isopropyliden glycerin and eugenol. This combination was found particularly suitable for obtaining concentrated sophorolactone compositions in liquid form. Such compositions may be used as such or are ready for use upon dilution with water.

Phenoxyethanol, benzyl alcohol, phenetyl alcohol, hydrocinnamylalcohol, dimethylisosorbide, methyl salicylate, 2-3-o-isopropyliden glycerin or eugenol as solvent for elevated amounts of sophorolactone were found to be particularly advantageous for the formulation of agrochemical and biocide products. The combinations provided a synergistic effect, in particular an improved effectiveness against microorganisms, such as bacteria, mould and yeasts.

In a preferred embodiment, an agrochemical or biocide formulation comprises an agrochemical or biocide active ingredient and at least 5 wt % sophorolactone, preferably at least 10 wt % sophorolactone, more preferably at least 15 wt % sophorolactone, most preferably at least 30 wt % sophorolactone, the remainder being solvent selected from the list of phenoxyethanol, benzyl alcohol, phenetyl alcohol, hydrocinnamylalcohol, dimethylisosorbide, methyl salicylate, eugenol, glycol ethers, Solketal, lactate esters, dimethyl lactamide, or combinations thereof. Most preferably the solvent is phenoxyethanol or benzyl alcohol.

The active ingredient is preferably a natural active ingredients, meaning not synthetically produced, such as rhamnolipids, laminarin, cinnamaldehyde, thymol, ammonium nonanoate, octanoic, nonanoic or decanoic acid, *Melaleuca alternifolia* oil, cedarwood oil or *Glycyrrhiza glabra* extract, extracts or infusions of *Chrysanthenum cinerariifolium, Artemisia absinthium, Tanacetum vulgare, Quassia amara* or *urtica* species or endotoxins of *Bacillus thuringiensis*. The sophorolactone enhances the activity of the active pesticidal ingredient by promoting the solubility, spreading and penetration of the active component, while being low foaming, non-toxic and biodegradable. Moreover it causes the formation of a hydrophilic lactone film incorporating part of the active ingredient and protecting it from being rinsed off by water or sweat. Such formulations may be used as such or after dilution in water.

This combination is particularly interesting as it provides a biodegradable surfactant in a GRAS-type solvent. By the term GRAS-type solvent, it is meant a solvent which is generally recognized as safe. These liquid sophorolactone formulations are particularly interesting as formulation auxiliaries for cosmetics, agrochemicals and biocides, where the environmental and toxicological profile of products is of particular importance. It provides improved consumer acceptance and safety.

The formulations may further be combined with other ingredients such as other solvents, surfactants and additives such as antioxidants. Preferably these ingredients are also generally recognized as safe. Preferred GRAS surfactants are sugar esters such as sucrose oleate or octanoate, sorbitol oleate or octanoate, and alkylpolyglucosides. Preferred GRAS solvents are lactate esters such as ethyl lactate or butyl lactate.

TABLE 1

Hansen Solubility Parameters for a selected range of solvents together with their capacity to dissolve sophorolactone; δD, δP and δH respectively stand for the dispersion parameter, polar parameter and hydrogen bonding parameter. They are expressed in $MPa^{1/2}$.

| Solvent | CAS n° | δD | δP | δH | % lactone dissolved | GRAS status |
|---|---|---|---|---|---|---|
| Water | 7732-18-5 | 15.5 | 16 | 42.3 | <1 | OK |
| Glycerol | 56-81-5 | 17.4 | 12.1 | 29.3 | <1 | |
| 1.3 propanediol | 504-63-2 | 16.8 | 13.5 | 23.2 | 2.75 | |
| Propylene glycol | 57-55-6 | 16.8 | 9.4 | 23.3 | 9.05 | |
| Caprylyl Glycol | 1117-86-8 | | 6.3 | 15.5 | 8.65 | |
| Ethanol | 64-17-5 | 15.8 | 8.8 | 19.4 | 7.5 | |
| Phenoxyethanol | 122-99-6 | 17.8 | 5.7 | 14.3 | 35.53 | NOK |
| Benzylalcohol | 100-51-6 | 18.4 | 6.3 | 13.7 | 67.35 | OK |
| Methanol | 67-56-1 | 15.1 | 12.3 | 22.3 | 8 | |
| Isopropanol | 67-63-5 | 15.8 | 6.1 | 16.4 | 2.2 | |
| Phenetyl alcohol | 60-12-8 | 19 | 5.8 | 12.8 | 22 | OK |
| Glycerin formal | 5464-28-8 | 16.37 | 11.99 | 19.63 | 35 | NOK |
| Ethylacetate | 141-78-6 | 15.8 | 5.3 | 7.2 | 3.96 | |
| Glacial acetic | 64-19-7 | 14.5 | 8 | 13.5 | 23.65 | |
| Diethylether | 60-29-7 | 14.5 | 2.9 | 5.1 | | |
| DPM | 34590-94-8 | 15.5 | 5.7 | 11.2 | 28.93 | NOK |
| PNP | 1569-01-3 | 15.8 | 7 | 9.2 | 15.57 | |
| PNB Henkel | 005131-66-8 | 15.3 | 4.5 | 9.2 | 6.73 | |
| Ethyllactate | 141-78-6 | 16 | 7.6 | 12.5 | 19.45 | OK |
| Isoamyl lactate | 19329-89-6 | 15.5 | 5.4 | 12.3 | 21.2 | NOK |
| D-limonene | 5989-27-5 | 13.2 | 1 | 4.7 | 8.5 | |
| Butyl lactate | 138-22-7 | 15.8 | 6.5 | 10.2 | 20 | OK |
| Hexanol | 111-27-3 | 15.9 | 5.8 | 12.5 | 2.65 | |
| Dimethyl lactamide | 35123-06-9 | | | | 65.64 | NOK |
| Dimethyl isosorbide | 5306-85-4 | 17.18 | 9 | 8.18 | 31.89 | NOK |
| Glycerincarbonate | 931-40-8 | 17.9 | 9.6 | 18.9 | <1 | |
| 2-3-o-isopropyliden glycerin | 100-79-8 | | | | 36.18 | NOK |
| Hydrocinnamylalcohol | 122-97-4 | 18.6 | 5.6 | 12.7 | 32.5 | OK |

The combination with sophorolactone was found to be particularly suitable for the control of pests.

A combination of sophorolactone with a polyol ester may be used for killing or knocking down a pest selected from the group consisting of cockroaches, ants, silverfish, firebrats, bristletails, wasps, hornets, crickets, earwigs, centipedes, scorpions, sowbugs, pillbugs, spiders, lice and mites.

A method of killing or knocking down the pest comprises spraying the pest with a formulation comprising a polyol ester selected form the list of sucrose oleate, sucrose octanoate, sorbitol oleate, sorbitol octanoate and sophorolactone.

Preferably the formulation comprises between 0.1 and 5 wt % of sophorolactone.

Preferably the pest is contacted with at least 1 gram of the mixture of polyol ester and sophorolactone.

Without being bound to theory, it is speculated that the synergistic effect of the ester/sophorolactone combination is due to the stickiness and film forming effect of the sophorolactone which enhances the contact of the product with the insect and reinforces the surfactants capability to dewax the insect's protective coating. The insect then either dehydrates or is readily attacked by ever present environmental microbes. The sucrose and sorbitol esters are readily biodegradable and hydrolyze to readily metabolizable sucrose or sorbitol and fatty acid. This is advantageous as it allows the compositions to be used as biopesticides. With the term biopesticides it is meant, pesticides derived from such natural materials as animals, plants, bacteria.

In a more preferred embodiment the formulation is non-aqueous and is based on non-flammable, such as phenoxyethanol, glycerin formal, dimethyllactamide, dimethylisosorbide or benzyl alcohol.

The formulation can be further complemented with surfactants, pest control agents such as benzyl benzoate or with insect repellants such as octanoic, nonanoic, or decanoic acid, or with citronella oil, geraniol, cedar oil and the like.

In a preferred embodiment the formulation is an insect repellant composition, the activity of which is prolonged in time due to the sophorolactone coating that withstands repeated rinsing or continues draining by water or sweat. The formulation consists of a sophorolactone and a non-flammable solvent according to this invention as well as an insect repellant such as octanoic, nonanoic, or decanoic acid, or with citronella oil, geraniol, cedar oil and the like. Such combination is especially suited when used on human or animal skin where sweat would otherwise quickly diminish the insect repellant effect.

In a further preferred embodiment an active component against Varoa mite, such as for example feromone 2-heptanone, is formulated in a sophorolactone solution of the invention and sprayed on the interior of beehives in order to provide for controlled release of the pheromone and a longer lasting effect against Varoa. 2-hepanone is a very volatile pheromone and will completely disappear from the treated beehive within 24 hours.

A composition according to an embodiment of the invention is especially suitable as starting material for obtaining a composition with a pre-determined foaming behavior. Addition of a selected amount of base equivalents, preferably at least 0.5 equivalents expressed relative to the lactone, provides a mixture of sophorolipids in lactone and acid form thereby increasing the foaming capacity of the formulation.

Alternatively, hydrolysis of the lactone can be obtained by heating the sophorolactone composition consisting of 70 wt %-99.9 wt % sophorolactone, 0-1 wt % sophorolipid acid, less than 0.1% residual substrate, and remainder water for more than 4 hours, more preferably more than 24 hours. The sophorolactone is heated to a temperature between 70-90° C., preferably to a temperature between 80-90° C.

This procedure hydrolyzes at least part of the sophorolactone providing sophorolipid acid and/or its salt. This has for effect that the foaming behavior is tunable by selection of the amount of base equivalents.

In a preferred embodiment, the base used for obtaining a partially hydrolyzed surfactant as described previously is guanidine or guanidinium hydroxide.

The hydrolysis will result in a composition comprising sophorolactone and sophorolipid in acid form with a guanidine counter ion.

Guanidinium hydroxide is generally prepared by mixing an inorganic alkaline earth hydroxide with an aqueous solution of a salt of the strong organic base guanidine, where the anion of this salt is capable of being precipitated by the cation of the alkaline earth hydroxide. Guanidinium hydroxide is generally prepared using calcium hydroxide and guanidine carbonate.

In a preferred embodiment, the base used for obtaining a partially hydrolysed surfactant as described previously is guanidine or guanidinium hydroxide. Preferably the resulting composition is used for the treatment of allergic reactions, preferably for the denaturation of proteins from arthropods such as dust mites.

It has now surprisingly been found that a composition comprising sophorolactones effectively reduces the allergic reaction to the excrements of house dust mites; particularly dust mite induced respiratory insufficiency.

In a preferred embodiment partial hydrolysates of sophorolipids with guanidinium counter ion are used to denature proteins. This is advantageous as the denaturing of proteins from animals, molds, pollens and dust mites contributes to allergies which are hard to treat.

Approximately 500 million people around the world are allergic to dust mites. Symptoms which may come from sensitivities to the dust mite protein include sneezing, congestion, itchy, watery eyes and persistently stuffy nose and ears. It is believed that allergy to dust mites may be a factor in 50% to 80% of patients with asthma as well as a numerous cases of eczema, hay fever, and other allergic symptoms. Dust mites are ubiquitous in homes, and thrive in beds, draperies and carpets. It is extremely difficult to remove them from the living environment and an allergic individual is constantly exposed to the allergen and such constant exposure may cause the allergic condition to worsen with time. Thus, allergy to dust mite may be chronic and difficult to treat.

House dust mite (Dermatophagoides) allergy is a hypersensitive reaction to proteins present in the excretion products of house dust mites and can result in respiratory insufficiencies such as airway obstruction and bronchial hyper reactivity. Such hypersensitive reaction is called "dust mite induced respiratory insufficiency" in the present document. House dust mites are found in almost all homes. The excretion products of dust mites can form a serious threat to those sensitive to said excretion products as well as to critically ill patients. The dust mites are not visible to the unaided eye, and thus difficult to detect in the house.

Allergic reactions caused by dust mite are known to be caused by dust mite proteins.

It has now surprisingly been found that a composition comprising sophorolactones denatures dust mite proteins. The denaturation of these proteins can be used to mitigate allergic reactions to dust mite proteins as it is capable of deactivating this allergen.

The invention provides a composition comprising sophorolactones for use in treatment and/or prevention of dust mite allergy. Preferably the composition is for human or veterinary use.

Partial hydrolysates of sophorolactones with guanidinium counter ion were found to be particularly suitable for the denaturation of proteins, particularly dust mite proteins.

The invention provides a composition comprising partial hydrolysates of sophorolactones with guanidinium counter ion for use in treatment and/or prevention of dust mite allergy in humans. Sophorolipids with guanidinium counter ion have an elevated pH, in particular a pH above 12, which was found particularly suitable for protein denaturation.

The invention further provides use of a composition or formulation according to an embodiment of the invention as deactivator for dust mite allergen. Preferably a composition according to an embodiment of the invention is used for the prevention, mitigation and/or treatment of allergic reactions, preferably for the denaturation of proteins from arthropods such as dust mites.

The invention further provides a method for treatment and/or prevention of dust mite allergy in a human or animal in need thereof, said method comprising administering a composition comprising sophorolactones, preferably also including partially hydrolyzed sophorolactones, more preferably including partial hydrolysates of sophorolactones with guanidinium counter ion, to said human or animal.

Whereas sophorolactones are low or non-foaming, hydrolyzed sophorolactones display increased foaming. Hence, a formulation may be obtained with desired foaming properties by adjusting the level of hydrolyzed sophorolactones accordingly.

A composition for treatment of mite allergens is preferably provided in the form of a shampoo.

In a preferred embodiment, the anti-lice composition comprises: 70 wt %-99.9 wt % sophorolactone, preferably at least 95 wt % sophorolactone, more preferably at least 98 wt % sophorolactone, most preferably at least 99 wt % sophorolactone, 0-1 wt % sophorolipid acid, less than 0.1% residual substrate.

It is speculated that the sophorolactone, due to its spreading, film-forming and sticky nature leaves a residue that contributes to prolonged effectiveness of an article treated with a sophorolactone composition against dust mites.

The invention further provides articles, such as carpets, curtains, bed linen, obtained by treatment with a composition according to an embodiment of the invention.

Compositions and formulations as described above can also be used for the treatment of acne or dandruff.

Sophorolactone and partially hydrolyzed sophorolactone compositions were found effective against the bacterium *Propionibacterium acnes*, a gram positive facultative anaerobe responsible for causing acne.

In a preferred embodiment, the composition further comprises a ligand selected from the list of poly-3-hydroxybutyrate (PHB) PHB-co-10%-3-hydroxyhexanoate (PHB/HHn), pectin and alginate. The former two worked best but created a more opaque film than pectin and alginate. The latter two are best suited for application to the facial areas.

Compositions and formulations as described above were found to be effective for the control of acne or dandruff causing organisms. They can advantageously be used for the formulation of composition for the treatment of acne or dandruff as they have an improved hydrolytic stability due to the substantial absence of acids. In addition their water content can be kept to a minimum. This has for effect that their effectiveness and foaming properties due not decrease substantially over time. This provides for more reliable and robust formulation auxiliaries.

In a further aspect uses are provided for the compositions and formulations of the inventions. In a preferred embodiment a composition or formulation according to an embodiment of the invention is used as formulation auxiliary for a household cleaning, industrial cleaning, cosmetic, agrochemical or biocide product, or as template for nanomaterial synthesis.

In another aspect a formulation is provided comprising between 50% and 95% of a composition sophorolactone composition and between 5% to 50% of a non-ionic surfactant, preferably a fatty alcohol alkoxylate, even more preferably an ethoxylate with a degree of ethoxylation below 8, wherein the sophorolactone composition comprises 70 wt %-99.9 wt % sophorolactone, 0-1 wt % sophorolipid acid, less than 0.1% residual substrate, and remainder water. This formulation has proven to remain stable at cold temperatures, particularly below 10° C., preferably below 5° C., which facilitates storage and handling. The formulation is of low viscosity, preferably of less than 1000 mPa·s.

In another aspect a formulation is provided comprising between 50% and 95% of a composition sophorolactone composition and between 5% to 50% of an anionic surfactant, preferably octyl sulphate, wherein the sophorolactone composition comprises 70 wt %-99.9 wt % sophorolactone, 0-1 wt % sophorolipid acid, less than 0.1% residual substrate, and remainder water.

In a preferred embodiment a composition or formulation according to an embodiment of the invention is used as a cleaning composition for hard surface cleaning. Preferably the surface is a glass surface such as a window.

Aluminum is a soft metal that easily corrodes in hot alkaline environments. The acidity or alkalinity of the environment significantly affects the corrosion behavior of aluminum alloys. At lower and higher pH, aluminum is more likely to corrode but by no means always does so. For example, aluminum is quite resistant to concentrated nitric acid. When aluminum is exposed to alkaline conditions corrosion may occur, and when the oxide film is perforated locally, accelerated attack occurs because aluminum is attacked more rapidly than its oxide under alkaline conditions. The result is pitting corrosion.

High purity grades of aluminum (±99.5%) and its alloys still are preferred for some food and pharmaceutical applications due to the reasonable corrosion resistance of the metal. This resistance is attributable to the easy and rapid formation of a thin, continuous, adherent oxide film on exposed surfaces. This oxide film, in turn, exhibits a good corrosion resistance to many foodstuffs; and it is reported that fats, oils, sugar, and some colloids have an inhibitory or sealing effect on these films. As aluminum salts formed by corrosion are colorless, tasteless, and claimed to be non-toxic—the metal is easy to clean, inexpensive, light, and has a high thermal conductivity. It still is used quite extensively in certain areas of food manufacture and distribution. Since modern plants operate on a semi-continuous basis with much higher levels of fouling, cleaning regimes require strongly alkaline detergents to which aluminum has virtually zero corrosion resistance.

The inventors have found that the compositions of the invention may advantageously be used to clean soft metal surfaces, such as aluminum. A method of cleaning aluminum objects with compositions of the invention may be used as an alternative to cleaning regimes using strongly alkaline detergents to which aluminum has virtually zero corrosion resistance. The method may also be suitable for treating other soft metals such as lead, tin, copper, zinc or alloys such as terneplate. Preferably the cleaning composition has a pH lower than 7.

In a preferred embodiment a composition or formulation according to an embodiment of the invention is used as a cleaning composition for cleaning soft metals such as aluminum, lead, tin, copper, zinc or alloys such as terneplate, and wherein the composition has a pH lower than 7.

In a preferred embodiment the rinse water of such cleaning process is treated with a fatty acid or an ester thereof to split the rinse water in three fractions, allowing for recovery of sophorolipids, removal and destruction of the oily layer and specialized treatment of the aqueous phase.

In a further preferred embodiment, the formulation auxiliary is for improvement of the wetting by water of the surface the product is applied to. Preferably the surface is a glass surface such as a window or the surface is a leave such as a leave of an agricultural crop.

In a preferred embodiment, the formulation auxiliary is for improvement of the rain fastness of the product. Preferably the product is an agrochemical product.

Since in practice sufficient time exists for spreading or wetting to reach equilibrium, the processes are determined by the equilibrium spreading coefficient, in turn determined by the reduction of the surface tension of the solution and the reduction of the substrate/solution interfacial tension. Since the substrates are mostly hydrophobic in nature, surfactants that will absorb onto the substrate in such fashion as to lower the substrate/solution interfacial tension are desired. Good dynamic wetting agents such as short chain and anionic surfactants foam too much or will cause too small particles resulting in spray drift and in loss of active material and uncontrolled application. Ideal droplet size is 200-300 micron, which is a compromise between aerosol drift reduction and leaf coverage or wetting. Sophorolactones are low foaming nonionic surfactants and excellent, multiple rinse resistant wetting agents. Contrary to acid sophorolipids, sophorolactone is insensitive to hard water. This is advantageous as hard water is often used in admixing adjuvants to a pesticide solution.

A common concern with agrochemical applied on vegetation is that efficacy can be reduced if rain falls shortly after spraying or other mode of application. This concern is more pronounced with chemicals that have moderate to high solubility in water.

An example of a foliar-applied agent whose efficacy is sensitive to the occurrence of rain shortly after application is the herbicide N-phosphono-methylglycine, also known by its common name glyphosate.

Glyphosate is a highly effective and commercially important herbicide useful for combating the presence of a wide variety of unwanted vegetation, including agricultural weeds. Glyphosate is applied as a formulated product to the foliage of annual and perennial grasses and broadleaf plants and the like, and is taken up over a period of time into the leave whence it translocates throughout the plant.

Glyphosate in ionic form has relatively high water solubility, especially when formulated as a salt, and during the uptake period immediately after application glyphosate is vulnerable to being washed off the foliage by rain or by overhead watering or irrigation. As glyphosate has practically no herbicidal activity in the soil, its efficacy is seriously reduced by such washing.

Another example of a suitable herbicidal active for combination with sophorolactone is ammonium nonanoate, a $C_9$ saturated-chain fatty acid soap salt, used for the suppression and control of weeds including: grasses, vines, underbrush, annual/perennial plants, including moss, saplings, and tree suckers. Ammonium nonanoate is used as a non-systemic, broad-spectrum contact herbicide. It has no soil activity, is rapidly biodegradable and degrades rapidly and will not persist in the environment.

For use, an ammonium nonanoate concentrate is diluted with water to a specified concentration. Application rates are up to a maximum concentration of 6.0% by weight, corresponding to 2.4% by weight ammonium nonanoate, in water. For the active ingredient to be effective, the leaves of undesirable vegetation must be uniformly sprayed and thoroughly wetted. Application can be repeated as often as necessary to obtain the desired control.

The length of time during which glyphosate is vulnerable to rain depends on many environmental and plant factors, and on the duration and intensity of rain, but can be as short as thirty minutes or as long as twelve hours or more after application. In the great majority of cases rain falling six or more hours after application does not seriously affect performance of the herbicide.

Usually, glyphosate is formulated in commercial compositions in the form of a water-soluble salt. Salts in commercial use include alkylamine salts, such as the isopropylamine salt, alkali metal salts, such as the sodium salt, the ammonium salt and the trimethylsulfonium salt. However, formulations of glyphosate in its acid form are also used. Typical glyphosate salt formulations include aqueous concentrates, requiring simple dilution in water for application by the end-user, and water-soluble or water-dispersible dry formulations, especially granules, requiring dissolution or dispersion in water prior to application. Most formulations, whether liquid or dry, also contain one or more surfactants. Even with such surfactants in the formulation there remains a need for enhanced rain fastness of glyphosate in many situations.

Mixtures of silicone-based surfactants and certain short-chain hydrocarbon surfactants are extensively used as adjuvants for agrochemical formulations to enhance the spreading properties of aqueous solutions on hydrophobic surfaces. Spreading factors (ie spreading area of 0.008 g of 0.1% (by wt) surfactant solution relative to the area spread by 0.008 g of deionized water on Parafilm after 1 min can be doubled from a factor of 15 for Silwet L-77 to a factor of 30 when using a 3:1 or 9:1 mixture of Silwet with a co-surfactant.

The ethoxylated siloxane surfactant Silwet L-77 has been the subject of research into rain fastness enhancement for glyphosate salt formulations. Its main active ingredient is 1,1,1,3,5,5,5-heptamethyltrisiloxanylpropyl-omega-methoxypoly (ethylene oxide) where the average number of ethylene oxide units is approximately seven. Other siloxanes of related composition are also described in the art. In addition to the high cost of Silwet L-77, common to all siloxanes, a number of disadvantages have been described, notably its tendency to antagonize the activity of glyphosate on some species in the absence of rain. The inventors have found that sophorolactone provides an interesting alternative. Sophorolactone provides improved spreading, wetting and rainfastness enhancement. Moreover it is environmentally friendly as derived from natural resources and easily biodegradable. With the controlled amount of acid in a sophorolactone composition according to an embodiment of the invention, sophorolactone hydrolysis is reduced significantly ensuring a prolonged non- to low-foaming behavior over time. This is essential in agrochemical applications as the application using spray nozzles for the application of a product wherein sophorolactone has hydrolyzed to the foaming sophorolipid acid form, would result in undesired amounts of foam. In addition sophorolactone is not phytotoxic.

In a preferred embodiment a storage-stable, liquid or water soluble agriculturally acceptable water soluble composition comprises:

(a) glyphosate or one or more of its salts or mixtures thereof, (b) a sophorolactone surfactant (c) 0-1 wt % sophorolipid acid, and (d) less than 0.1% residual substrate.

In a preferred embodiment, the agrochemical or biocide product is for post-harvest protection of fruit, cereals or vegetables.

In a preferred embodiment, a method for providing protection to fruit, cereals or vegetables comprises the step of contacting the fruit, cereals or vegetables post-harvest with a solution comprising sophorolactone and a solvent generally recognized as safe (GRAS solvent).

Sophorolactone was found to be particularly suitable for the post-harvest protection of fruit, cereals or vegetables. In a preferred embodiment the sophorolactone is dissolved in a GRAS-type solvent according to the invention such as benzyl alcohol, ethyllactate, butyllactate or hydrocinnamyalcohol.

These liquid sophorolactone formulations are particularly interesting as formulation auxiliaries for cosmetics, agrochemicals and biocides, where the environmental and toxicological profile of products is of particular importance. It provides improved consumer acceptance and safety.

The formulations may further be combined with other ingredients such as other solvents, surfactants and additives such as antioxidants. Preferably these ingredients are also generally recognized as safe. Preferred GRAS surfactants are sugar esters such as sucrose esters, sorbitol esters or alkylpolyglucosides. Preferred GRAS antioxidants are ascorbic acid or isoascorbic acid.

In a preferred embodiment, the agrochemical formulation is for seed coating, soil disinfection, slug or snail baiting.

In a preferred embodiment, the agrochemical or biocide product is for insect repellant treatment of human skin, animals, stable walls and so forth.

In a preferred embodiment, the agrochemical or biocide product is a deodorant using actives against microorganism growth thus preventing odor development. Such actives include for example farnesol and triethylcitrate. Applying such actives as part of a formulation with sophorolactone dissolved in a solvent, itself active against microorganism will enhance the product performance. The sophorolactone coating on the skin will furthermore protect the active from being drained away with sweat and in doing so will prolong the activity of the deodorant. Treated underarm hair is thought to wick the moisture away from the skin and aids in keeping the skin dry enough to prevent or diminish bacterial colonization. The hair is less susceptible to bacterial growth and therefore is ideal for preventing the bacterial odor. The deodorant may alternatively or may further contain antiperspirants such as aluminium chloride, aluminium chlorohydrate, and aluminium-zirconium compounds, most notably aluminium zirconium tetrachlorohydrex gly and aluminium zirconium trichlorohydrex gly. The deodorant composition comprises 0.1-2% sophorolactone, 0-5% biocide, 0.2-3% fragrance, 0-30% antiperspirants such as aluminium salts, the remainder being solvent or solvent mixtures such as water or ethanol and water.

In a preferred embodiment, the slug bait composition comprises 0.5-10% carbamate on a 30-70% carrier, 10-70% of a food substrate, such as ground cereals, starch or flour, and 0.5-10% sophorolactone.

In a further embodiment, the cosmetic product is a shampoo and the formulation auxiliary is for foam enrichment.

Preferably the composition or formulation according to an embodiment of the invention is used as a wire drawing composition, wherein the composition has a pH below 7.

Preferably the composition or formulation according to an embodiment of the invention is used as a lubricant additive.

In another embodiment of the invention a sophorolactone composition or formulation according to an embodiment of the invention, is used for surfactant assisted nanomaterial generation.

A process for the preparation of nanoscale particulate material comprises the steps of: combining one or more functional material to be precipitated as nanoscale particles and a sophorolactone composition, mixing the functional material and the sophorolactone composition thereby providing micelles, providing reaction conditions for formation of nanoscale particulate material, growing nanoscale particulate material using the micelles as templates, and collecting the nanoscale particulate material.

Nanoscale particulate materials are defined as substances with particulate dimensions that are on the order of up to 0.1 µm. In the case of symmetric materials such as spherical particles, the particle diameter is the defined quantity while in the case of anisotropic materials such as rods, fibers or plates, at least one of the three axial dimensions is required to be in the defined size range. The sophorolactone composition provides templates in the form of micelles which act as templates for the synthesis of nanomaterials. The interaction of the surfactant micelles with functional material provides a way to the nucleation and growth of nanostructures.

In a final aspect of the invention, a method is provided wherein a surfactant composition or a formulation according to an embodiment of the invention, are used for cleaning. In particular, a method is provided for removing oily waste from an object in need of cleaning. The method according to an embodiment of the invention comprises the steps of:

providing a surfactant composition or a formulation comprising the surfactant composition according to an embodiment of the invention, cleaning the object with the surfactant composition or the formulation thereby generating rinse water comprising sophorolipids and the oily waste, and separating the sophorolipids and/or oily waste from the rinse water.

The possibility to recover sophorolipids and/or oily waste from the waste water is advantageous as it allows the reduction of waste. The sophorolipids and/or oily waste can be valorized by use in other applications. Such a method is particularly useful for the recovery of valuable materials from cleaning operations involving slaughter house waste.

The invention is further described by the following non-limiting examples which further illustrate the invention, and are not intended to, nor should they be interpreted to, limit the scope of the invention. It is supposed that the present invention is not restricted to any form of realization described previously and that some modifications can be added to the presented example of fabrication without reappraisal of the appended claims.

EXAMPLES

Example 1: Film Forming Properties

A solution of 10% sophorolactone in benzyl alcohol was applied to a PVC sheet and allowed to air dry. This resulted in a glossy dry layer which was virtually impossible to remove with running tap water or with repeated rinsing with water. This experiment was repeated with pieces of leek with the same outcome.

Example 2: Film Forming Properties

Ten percent of a solution of a 10% sophorolactone solution in ethanol was dispersed in water to obtain a white 1% sophorolactone dispersion. The dispersion remained stable overnight at room temperature without visual separation. Immersing a PVC sheet into this dispersion or applying the dispersion onto the strip and allowing to air dry resulted in a layer similar to that of Example 1 and withstanding at least 5 repeated rinse and dry cycles.

Example 3: Wetting and Film-Forming Behavior Test

A test composition was made by dissolving 10% sophorolactone in ethanol. The ethanolic lactone solution was diluted to obtain a 1% dispersion in deionized water (AD).

Different substrates are wetted with said 1% lactone dispersion and dried in a climate chamber at 40° C. Substrates used were glass, polyvinylchloride (PVC) and leek leaves.

Contact angles of deionized water on the treated substrate were measured with a DSA100 tensiometer (Krüss GmbH) and compared with the untreated substrate. Several contact angle measurements were performed on each substrate. The substrates are subsequently rinsed under running tap water during 20 seconds, allowed to dry at 40° C. and the contact angle is measured again. This rinse-dry-measure cycle is repeated for 5 times unless the contact angle notably increased prior to these 5 rinses.

The results obtained were for solutions wherein lactone was replaced by sodium lauryl sulphate (SPS), APG600 (a C10-C16 alkylpolyglucoside), wild type or crude sophorolipid (as obtained after fermentation, denominated as WT in Table 2), FAEO/PO nonionic (CAS 68439-51-0, C12-14 fatty alcohol, 5 mole EO, 4 mol EO), modified FAEO/PO (C8/10 fatty alcohol+1 PO+22 EO (2-hydroxydecyl)-ether) and siloxane polyether copolymer (Silwet Hydrostable 68).

This experiment was repeated with different substrates and different 1% active surfactant solutions as elaborated in Table 2.

As evident from this table treatment of all substrates with a 1% sophorolactone dispersion resulted in flat drops, the contact angle of which was so low ("NM", not measurable) that the apparatus could not properly determine it. Lactone solutions on hydrophobic surface such as PVC and leek resulted in excellent wetting by water even after 5 rinses, with in fact a lower contact angle after the first rinse than for just after the application of the dispersion.

TABLE 2

Experimental results of contact angle measurements, without or with rinses.

| Substrate | Product | Contact Angle | Rinse 1 | Rinse 2 | Rinse 3 | Rinse 4 | Rinse 5 |
|---|---|---|---|---|---|---|---|
| glass | blank | 49 | | | | | |
| PVC | blank | 90 | | | | | |
| Leek | blank | 64 | 64 | | | | |
| | | 75 | 65 | | | | |
| | | 73 | | | | | |
| | lactone | 28 | 25 | 10 | | | |
| | | 27 | 26 | NM | | | |
| | | 25 | 28 | 10 | | | |
| | WT | NM | 8 | 69 | | | |
| | | NM | 11 | 65 | | | |
| | | NM | NM | 61 | | | |
| PVC | WT | 18.1 | 79 | 80.5 | | | |
| | | 19.5 | 82 | 58 | | | |
| | | 24.3 | 72 | 76 | | | |
| glass | WT | 7.5 | 58.7 | 60.5 | | | |
| | | NM | 57.3 | 58 | | | |
| | | NM | 56.3 | 61 | | | |
| PVC | WT | NM | 59 | 90 | | | |
| | | NM | 54 | 87 | | | |
| | | NM | 72 | 90 | | | |
| | lactone | NM | 2 | 8.4 | NM | | |
| | | NM | NM | 16 | NM | | |
| | | NM | 4 | | NM | | |
| | | 20 | | | | | |
| | | 13 | | | | | |
| | 50/50 Lactone/WT | NM | 57.2 | 93 | 99 | | |
| | | NM | 29.2 | 81 | 95 | | |
| | | NM | 12.5 | 72 | 75 | | |
| | | 13 | | | | | |
| | | 59.2 | | | | | |
| glass | SLS | 11.3 | 7.2 | 33.2 | 37.3 | 50.8 | 34 |
| | | NM | 16.8 | 64.2 | 40.3 | 36.2 | 38 |
| | | 8 | 18.1 | 33.8 | 51.8 | | 30 |
| | | 8 | | | | | |

TABLE 2-continued

Experimental results of contact angle measurements, without or with rinses.

| Substrate | Product | Contact Angle | Rinse 1 | Rinse 2 | Rinse 3 | Rinse 4 | Rinse 5 |
|---|---|---|---|---|---|---|---|
| PVC | APG600 | 14 | 30 | 97 | | | |
| | | 19 | 8.2 | 78 | | | |
| | | 20 | NM | 83 | | | |
| | | | NM | 93 | | | |
| PVC | Lactone | 7 | 0 | 0 | 10 | NM | NM |
| | | 10 | 10 | 0 | 2 | NM | 9 |
| | | 10 | 7 | 0 | NM | NM | NM |
| PVC | 0.1% Lactone | NM | 66 | 90 | | | |
| | | NM | 67 | 80 | | | |
| | | NM | 79 | 80 | | | |
| glass | Lactone | 14.2 | 15.3 | 24.4 | 23.5 | 10.8 | 15.1 |
| | | 14.1 | 10 | 30 | 27.8 | 25 | 10.6 |
| | | 11.3 | 12 | 25 | 25 | 24 | 17.6 |
| | | 10 | | | | | 22.3 |
| PVC | SLS | 1 | 72 | 102 | 64 | 75 | 100 |
| | | 1 | 100 | 94 | 65 | 84 | 99 |
| | | 1 | 96 | 90 | 64 | 102 | 101 |
| PVC | Lactone in hard water* | 23 | 19 | 14 | 12 | 11 | 12 |
| | | 27 | 20 | 15 | 17 | 12 | 11 |
| | | 12 | 21 | 14 | 14 | 12 | 10 |
| PVC | WT in hard water* | 26 | 104 | | | | |
| | | 27 | 105 | | | | |
| | | 18 | 105 | | | | |
| PVC | EO/PO nonionic (averaged over 3 values) | NM | 15 | 35 | 45 | 35 | 35 |
| PVC | Modified EO/PO (averaged over 3 values) | NM | 14 | NM | 15 | 30 | 37 |
| PVC | Siloxane | NM | NM | 70 | 90 | | |

NM stands for not measurable due to an extremely low contact angle.
*hard water = a 10% lactone or WT solution was dispersed in hard water (200 ppm CaCO₃) so as to obtain a 1% active substance dispersion as in the other experiments Wild type sophorolipids (WT) are a mixture of nonionic (sophorolipids in lactone form) and anionic (sophorolipids in acid form) surfactants and tend to form, very much like the tested anionic sodium lauryl sulphate and like APG600, a patchy layer on the substrate, resulting in heterogeneous contact angle measurements. Moreover the anionic surfactant layer is completely or almost completely removed after two rinses as evidenced by the contact angles that approach that of the untreated substrate.

Alkoxylated surfactants, in particular the tested FAEO/PO and modified FAEO/PO, persisted several rinse cycles as well, although the contact angles after the first rinse were substantially higher than with sophorolactone, i.e. these surfactants are less prone to rinsing off.

A 1% lactone dispersion was made using hard water, resulting in equally low contact angles and excellent rinse resistance. An anionic surfactant, such as sophorolipids in acid form and sodium lauryl sulphate are prone to interference by calcium and calcium salts of the respective surfactant.

Example 4: Film-Forming Behavior Test with an Added Active Component

Example 2 was repeated, adding thymol to the ethanolic solution (10% lactone, 10% thymol and 80% ethanol) as model compound for a pesticide, thymol being known for its antiseptic activity. Ten percent of the ethanolic solution was dispersed in water to obtain a white 1% dispersion remaining stable overnight at room temperature without visual separation. Immersing a PVC sheet into this dispersion or applying the dispersion onto the strip and allowing to air dry resulted in a sticky layer, withstanding repeated rinse and dry cycles. Thymol remained fixed on the PVC substrate for several rinses as evidenced by the smell of the PVC as well as by the orange color after treating the PVC with concentrated sulfuric acid. The latter destructive detection method necessitated several PVC strips to be used, each strip lasting an extra rinse cycle before detection.

In the blank 1% thymol solution, the thymol formed a supernatant oily layer rather than a homogeneous solution or dispersion so this test was abandoned. A blank with lactone but without thymol produced brown rather than orange staining with sulfuric.

Reducing the concentration of thymol to 0.5% and 1% lactone resulted in a homogeneous dry coating of the PVC with the same reported water fastness.

From this model experiment the inventors conclude that it is possible to use sophorolactone to allow for excellent wetting of a hydrophobic substrate allowing maximal and intimate contact of an active such as a pesticide or an antiseptic agent with the treated substrate, and preventing the active to be washed off with water. Suitable substrates are plastics, plant material, keratin and hydroxyapatite.

Example 5: Rinse Aid Composition for Automatic Dishwashing

A rinse aid with the following composition, expressed as 100% active matter, 3.6% partially hydrolysed sophorolipids (0.7 mole equivalent), 5% citric acid, 2% ethanol, 0.7% alkylpolypentoside (C8/10), remainder water, was tested for its rinse performance on a Zanussi ZDF211 machine, allowing for five minutes drying after opening the machine after the D 50° C. Eco program was finished. A second formula was tested with the same composition but with 4.3% partially hydrolysed sophorolipids.

These compositions were compared to a market reference rinse aid and to the IEC436 Reference rinse aid formula III. The number of remaining water drops were counted and rated according to the method as described in the Schirmer W, Altenschöpfer T, Wichelhaus W, Andree H, Tenside Surf. Det. 28(5):313-319, 1991; herein incorporated by reference. The following rating was used: 0 drops=6 points; 1 drop=5 points; 2 drops=4 points; 3 drops=3 points; 4 drops=2 points; 5 drops=1 point; >5 drops=0 points, The maximum number of points to earn are: Total=192; Porcelain=42; Glass=72; Plastic=30; Metal=48. The results are presented as: (earned points/max points)×100.

Figure 2:
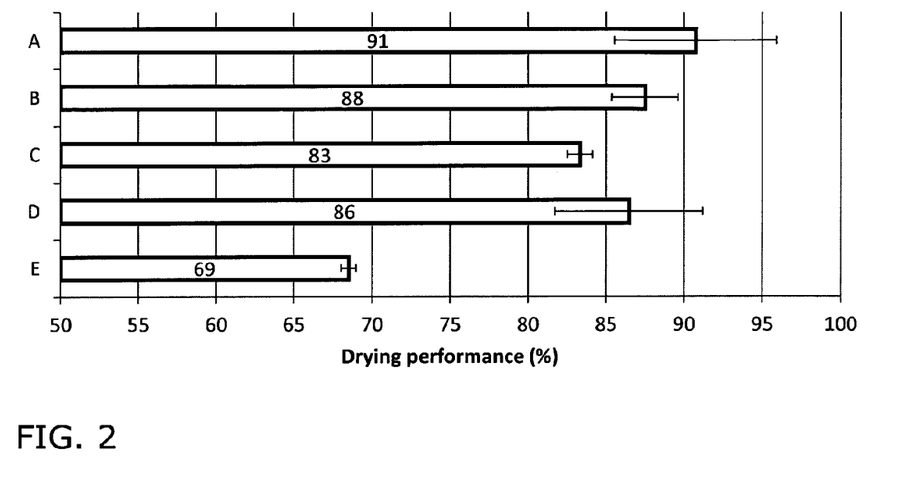
FIG. 2 is a graphic representation comparing the drying performance of rinse aid compositions applied on a hydrophobic surface, in particular on porcelain. Sophorolactone based formulas according to an embodiment of the invention (B, C) are compared to a market reference (A), an IEC436 reference rinse aid, form III (D), and a blank of water (E).

The results are depicted in FIG. 2, displaying the performance of the rinse aid on porcelain. As evident from this graph 4.3% active matter of partially hydrolysed sophorolipids (B) sufficed to match the performance of the IEC reference (D) as well as the market reference (A).

Example 6: Alternative Rinse Aid Compositions for Automatic Dishwashing a composition with 10% sophorolactone, 5% amyl lactate and 85% ethanol.

a composition with 10% sophorolactone, 5% ethylhexyllactate, 45% dipropylene glycol methyl ether and 40% dimethylisosorbide.

Example 7

A sophorolipid lactone sample comprising approximately 50% water and 0.1% cell fragments next to sophorolactone, was centrifuged, spread out on Torck paper and allowed to air dry. The resulting solid was crushed with a coffee mill to a fine powder and dried further with compressed air to >98 wt %. This powder was compared as to its efficiency in automatic dishwashing versus a low foaming alkylpolyglucoside, in particular Simulsol AS48, available from Seppic SA, at equal active matter content. The surfactant was formulated in the following base formula: 9.43% sodium citrate.2H$_2$O; 3.08% percarbonate; 2.72% sodium carbonate; 2.05% sodium silicate; 1.05% sodium bicarbonate; 0.77% sodium polyaspartate; 0.62% TAED+1.4% surfactant. 20 gram of the base formula was dosed in a ZDF211 dishwasher. Program D 50° C. eco was run.

In the automatic dishwasher 7 types of soil plates (available from CFT, Vlaardingen, The Netherlands) mounted in a stainless steel holding frame were inserted. The results obtained are summarized in Table 3.

TABLE 3

Stain removal efficacy for Simulsol AS48 compared to lactone for a series of stains.

| Stain | Cheese DM06 | Egg yolk/milk DM31 | Mix starch DM77 | Coffee DM81 | Tea DM11 | Red wine DM51 | Chocolate DM75 |
|---|---|---|---|---|---|---|---|
| Simulsol AS48 | | | | | | | |
| average Rs | 25.4 | 44.8 | 35.9 | 69.8 | 61.6 | 56.3 | 17.8 |
| average Rw | 40.0 | 51.2 | 39.2 | 77.9 | 75.2 | 72.2 | 24.0 |
| soil removal | 14.6 | 6.4 | 3.3 | 8.1 | 13.6 | 16.0 | 6.2 |
| Lactone | | | | | | | |
| average Rs | 25.0 | 45.1 | 36.0 | 70.2 | 61.1 | 55.3 | 17.8 |
| average Rw | 41.9 | 52.0 | 37.6 | 77.5 | 75.7 | 72.4 | 24.9 |
| soil removal | 16.9 | 6.8 | 1.6 | 7.3 | 14.6 | 17.1 | 7.1 |

Rs = Y reflection value for soiled;
Rw = Y reflection value for washed

As evidenced from the above soil removal rates, sophorolipid lactone, although virtually insoluble as such, was superior to Simulsol AS48. It is assumed the alkaline pH of about 9.8 caused in situ hydrolysis providing an efficient surfactant.

Example 8: Aluminum Cleaning Composition

Figure 3:
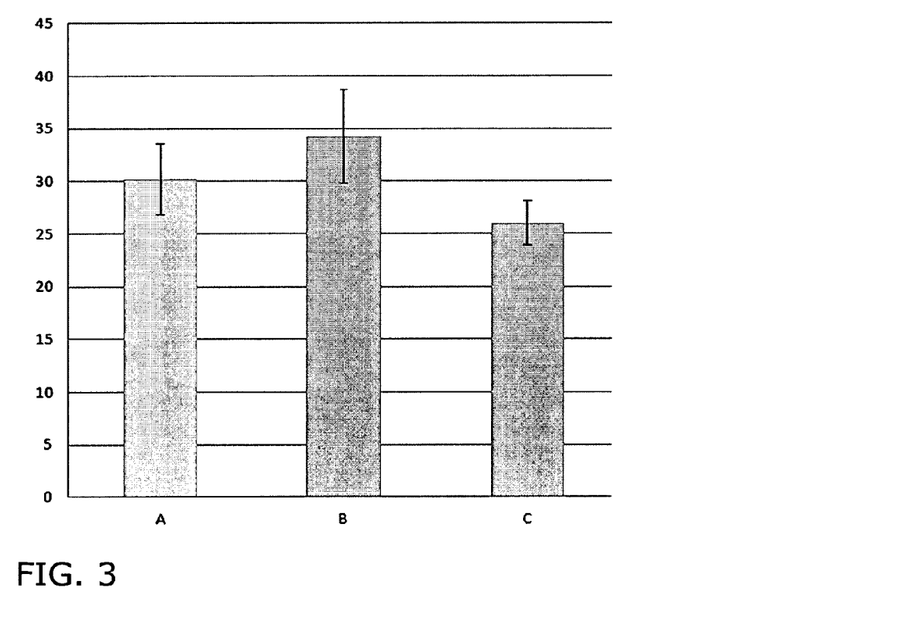
FIG. 3 is a graphic representation of the performance, expressed as Y-reflection values, of aluminium cleaning compositions according to an embodiment of the invention (A, B) as compared to a market reference product C.

Two products according to an embodiment of the invention, denominated (A and B on FIG. 3, based on partially hydrolysed (0.7 ratio) sophorolactone compositions were tested for their hard surface cleaning efficacy as compared to a market reference product for cleaning aluminum (product C). The sophorolipid product had a pH of 6.25 whereas the market reference product had a pH of 12.1, thus necessitating the use of corrosion inhibiting phosphorous and silicate components.

White PVC strips (Leneta) are soiled with a mixture of oils and carbon black. 10 ml of the product is put on the strip, 6 ml on a wet sponge. The sponge is mounted on Gardner scrub tester and is taken 10 times back and forward over the soiled strip at room temperature. The strip is rinsed during 30 s. After air-drying, the cleaned strips are measured with a reflectometer (Braive). The Y-value is reported and results are statistically evaluated with the software Statistica and visualised in FIG. 3.

A: contains 3.38% active matter sophorolactone composition, brix 9.5
B: contains 0.9% active matter sophorolactone composition, brix 18
C: comparative example, HG aluminium cleaner, brix 16.8 with formula
  phosphoric acid (diphosphoric acid, tetra potassium salt) 5-15
  C10 alcohol ethoxylate 1-5%
  disodium metasilicate 1-5%
  decyl polyglucose 1-5%

As evident from FIG. 3, there is no need to operate at high pH in order to achieve good cleaning of aluminium. Operating at lower pH sophorolipids allow sufficient cleaning, while reducing the risk for metal corrosion.

Figure 4:
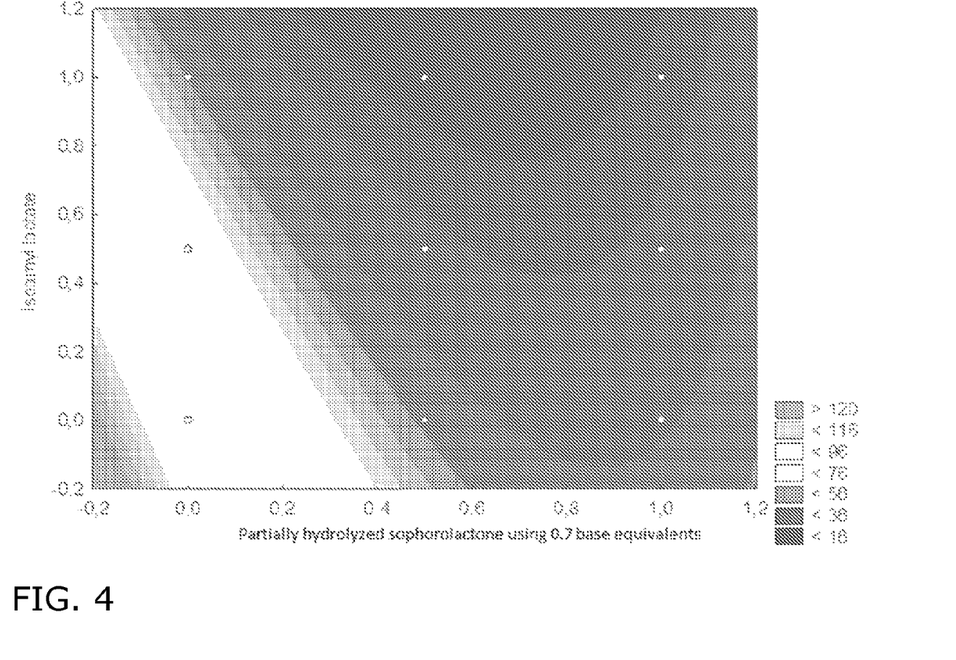
FIG. 4 is a graphic representation of contact angle measurements of mixtures of sophorolactone in isoamyl lactate as measured on white PVC-stripes. On the X- and Y-axis are displayed the concentrations of both ingredients ranging from 0 to 1% active matter each. Gray scale values depict the contact angle readings as measured by a Küss tensiometer DSA100, using the sessile drop method, at a temperature of 20° C.

Example 9: Contact Angle and Hard Surface Cleaning Performance of a Composition According to an Embodiment of the Invention Comprising Sophorolactone and Isoamyl Lactate Solvent The contact angle of combinations of isoamyl lactate (Galactic) with partial sophorolipid hydrolysate (0.7 mol equivalent) on white PVC-strips (Leneta) was measured at room temperature with a Krüss DSA100 tensiometer using the sessile drop method. Each component of the mixtures is at maximum 1% active matter. Results are evaluated with the software Statistica. As evident from the graph in FIG. 4, the use of amyl lactate allows to further improve the performance of amyl lactate and vice versa, with maximal PVC wetting at about 0.6% sophorolipid and 1.2% amyl lactate, the solubility of which is limited to 1% in water.

Example 10: Window Cleaning Composition

A composition according to an embodiment of the inventions suitable for cleaning glass surfaces, preferably windows, is as for example as depicted in Table 4.

TABLE 4

Example of a window cleaning composition according to an embodiment of the invention

| Composition | |
| --- | --- |
| Water | 93.70 |
| Dipropylene glycol methyl ether | 2.00 |
| Ethanol | 5.00 |
| Sophorolactone | 0.15 |
| Lactic acid | 0.02 |
| Lactate | 0.01 |
| Perfume | 0.12 |

Example 11: Antifogging Composition

One half of a mirror was treated with a 10% solution in water of a 10% solution of sophorolactone in ethanol and allowed to dry. The other half of the mirror was treated with a 10% solution of ethanol. Once dried the mirror was held above boiling water to observe any condensation or fogging effects. The treated part was not visually covered with condensation water and retained its mirror properties, whereas the untreated part was completely covered with condensation water.

In a preferred embodiment of the invention the treated surface is glass or plastic foil. The antifogging composition as described above is applicable to foil for food packaging, glass houses, shower cabins, and the like.

Example 12: Agrochemical Composition

N,N-dimethyl lactamide, sophorolactone, cyproconazole

Example 13: Antibacterial Fruit & Vegetable Wash

Water, lactic acid, lactate, benzyl alcohol, ethanol, grapefruit oil terpenes, lactone, ascorbic acid

Example 14: Antibacterial Fruit & Vegetable Wash

Water, lactic acid, ethyl lactate, grapefruit oil terpenes, lactone

Example 15: Deodorant

A deodorant with a pH of 5-5.5 was formulated using % 70 ethanol, 26.2% water, 2% triethylcitrate, 0.6% lemongrass oil, 0.6% bergamot oil, 0.2% sophorolactone, 0.2% lactic acid, 0.1% lactate.

Another deodorant was formulated using 90% ethanol, 5.9% phenoxyethanol, 1% decyl almond ester, 2% fragrance mix, 0.5% farnesol, 0.1% sophorolactone.

Both products remained physically stable in the climate chamber at 40° C. during 4 weeks, with no discoloration or phase separation and no sticky feeling to the skin even after repeated application.

Example 16: Anti Mite/Lice Concentrate/Shampoo

Lactone, CaCl2, benzyl alcohol, benzyl benzoate, farnesol, and optionally cedar oil

Example 17: Seed Coating Product

The sophorolactone can be used in aqueous solution for film-coating a seed of the proteaginous pea type (Ascona variety). The pea seed, which may or may not have received a plant health treatment, is film-coated with a film-coating machine of trademark HEGE, which is based on the principle of spraying the substances at very high speed on to a mass of seeds rotating about an axis; this causes an eccentric displacement, ensuring perfect intimacy between the seed and the film-coating products.

This method is used to prepare a batch of 500 g of pea seeds, film-coated with 4 ml of an solution of sophorolactone, having a content of 5% and completed with a dispersant for improving the product/seed contact.

This composition for film-coating seeds thus has an accelerating action on seed germination and plantlet growth.

Example 18: Foam Enrichment

A shampoo frame formulation was made using 3% partial sophorolipid hydrolysate (0.7 mole equivalent), 12% Plantapon SF (a proprietary blend to Cognis GmbH of sodium coamphoacetate, glycerin lauryl glucoside, disodium cocoyl glutamate and sodium lauryl glucose carboxylate) and 1.5% Lamesoft PO65 (a proprietary blend to Cognis GmbH of cocoglucoside and glyceryl oleate). Stirring this shampoo and comparing the obtained foam to a shampoo without sophorolipids surprisingly led to the conclusion sophorolipids enhance the creaming of the foam, with a more creamy, more stable yet easier to rinse off foam than the shampoo without sophorolipids.

Example 19: Sophorolipid Compound

Crude sophorolipid paste containing in excess of 70% sophorolactone was mixed with a second surfactant to obtain a lower viscosity compound.

1, 2, 5, 10 and 20 gram of the surfactants listed in Table 5 were added to 100 gram of sophorolipid paste, mixed and stored for 24 hours at 4° C. to evaluate the physical state after cooling. It was observed that upon stirring the crude paste became rather fluid suggesting a certain degree of thixotropy. Upon standing or cooling the product became pasty again.

The pH of the mixture with APG was adjusted to pH 5 using citric acid. Of all samples only the sample with 20 gram Texapon 842 and the sample with 20 gram Marlipal 24/30 added were translucent and remained so after storage at 4° C. The sample with Dehydrol LT7 was translucent at room temperature but became opaque after storage at 4° C. due to the higher pour point of the nonionic. The samples containing approximately 17% Texapon or Marlipal remained liquid with a viscosity of less than 1000 mPa·s, whereas all other samples became pasty displaying a viscosity in excess of 10000 mPa·s. Other ethoxylates have a lower pour point e.g. Marlipal 24/50 ca. 8° C. or Dehydrol O4 ca 2° C.

TABLE 5

Selections for use as a second surfactant in a composition according to the invention.

| Brand name | supplier | % active matter | INCI name | Surfactant class |
|---|---|---|---|---|
| Glucopon 215 CS UP | Cognis | 62-65% | Capryl glucoside | Nonionic surfactant |
| Radia Easysurf 6505 | Wheatoleo | 55-65% | Amyl xyloside | Nonionic surfactant |
| SCS | Manro | 40% | Sodium cumene sulphonate | Anionic surfactant |
| Marlipal 2430 | Sasol | 99.7-100% | Fatty alcohol ethoxylate (C12-14, 3EO) | Nonionic surfactant |
| Dehydol LT7 | Cognis | 99.7-100% | Fatty alcohol ethoxylate (C12-18, 7EO) | Nonionic surfactant |
| Texapon 842 | Cognis | 42% | Octyl sulfate | Anionic surfactant |

Example 20

A solution of 8 g partially hydrolysed sophorolipids (0.7 mole equivalent, 45% active) was made with 84 g water and 8 g caprylic/capric triglyceride (Myritol 318) to simulate rinse water of a cleaning process where a vegetable oil was removed by a sophorolipid based cleaner. The pH was adjusted to pH 6.5 using lactic acid.

A comparative solution was made with 4 g partially hydrolysed sophorolipids and 4 g alkylpolyglucosides ($APG_{10-16}$, Glucopon 600).

To both solutions varying amounts of oleic acid were added. Any changes were noted down. The results are provided in Table 6 below. The test was repeated with methyl oleate and rapeseed oil.

Using a near pH neutral solution of partially hydrolysed sophorolipid to clean a surface soiled with oil or fat and subsequently adding fatty acid or a ester thereof to the rinse water allowed for a split of the cleaning solution into 3 layers, i.e. a supernatant oily layer that was discarded, an intermediary aqueous layer that was treated and reused, and a bottom layer of sophorolactone, which was removed by decantation and was reused. The added fatty acid or ester thereof contributed to the cleaning efficacy.

TABLE 6

| | Comparative examples | |
|---|---|---|
| | Example | Comparative solution |
| Myritol 318 | 8 g | 8 g |
| Sophorolipid | 8 g | 4 g |
| APG | 0 g | 4 g |
| Water | 84 g | 84 g |
| Oleic acid 0.5 g | 3 phases, lactone bottom layer | 2 phases, no bottom layer |
| Oleic acid 0.25 g | 3 phases, lactone bottom layer | 2 phases, no bottom layer |
| Oleic acid 0.05 g | 3 phases, lactone bottom layer | 2 phases, no bottom layer |
| Rapeseed oil 0.5 g | 2 phases, no bottom layer | 2 phases, no bottom layer |
| Methyl oleate 0.05 g | 3 phases, lactone bottom layer | 2 phases, no bottom layer |
| Ethyl oleate 0.05 g | 3 phases, lactone bottom layer | 2 phases, no bottom layer |

Example 21: Storage Stability Test

Figure 5:
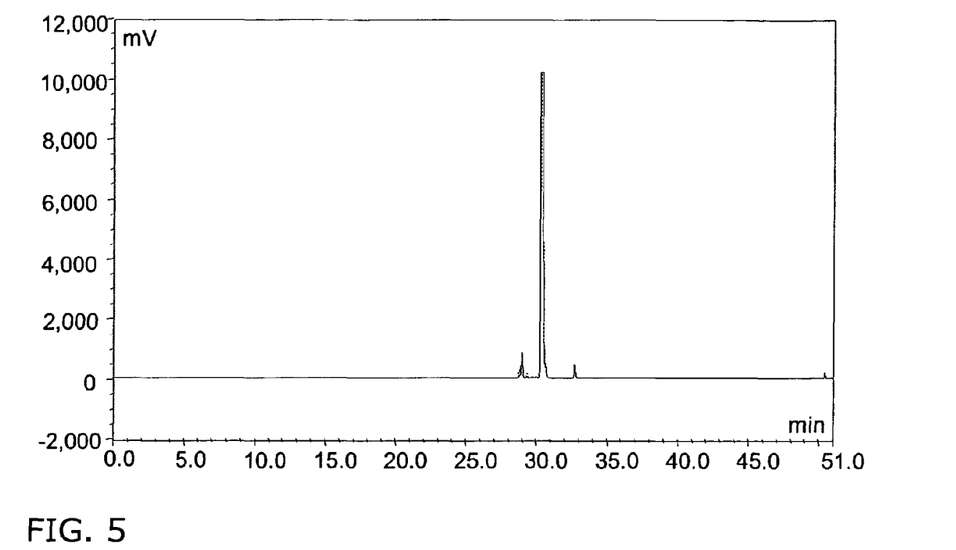
FIG. 5 is graphic representation of a chromatogram recorded on a non-aqueous sophorolactone solution prior to storage (black curve) and after storage (grey curve) at 4° C. for 2 months. Both curves practically overlap. The solution is storage stable as demonstrated by the virtual absence of a peak at a retention time of 30.5 min. in the grey overlay graph which would demonstrate the presence of acid sophorolipid, derived from hydrolyzed lactones.
Figure 6:
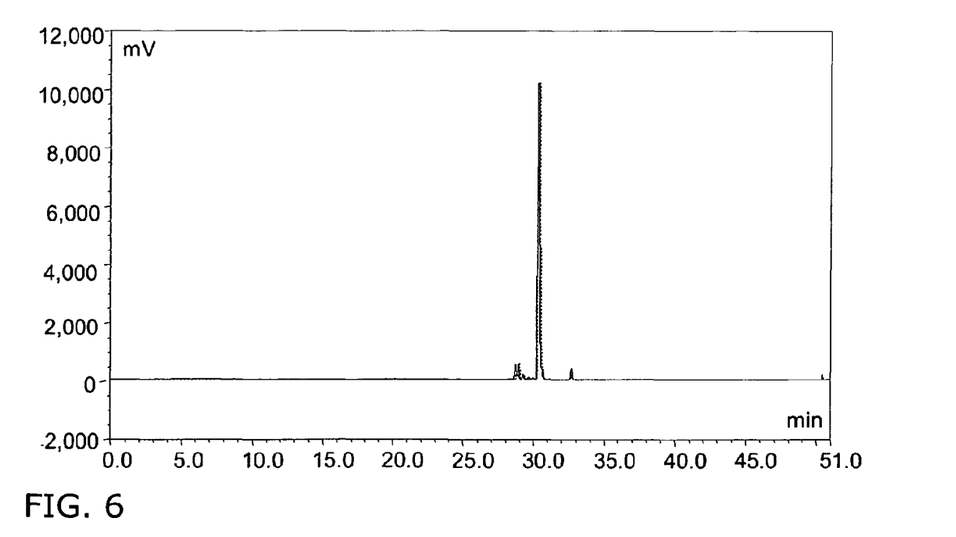
FIG. 6 is graphic representation of a chromatogram recorded on the same sample as for FIG. 5, after 2 months of storage at 40° C. Both curves practically overlap. The solution is storage stable as demonstrated by the virtual absence of a peak at a retention time of 30.5 min. in the grey overlay graph which would demonstrate the presence of acid sophorolipid, derived from hydrolyzed lactones.

A sample was prepared of 10 g sophorolactone and 90 g ethyllactate and another sample of 10 g sophorolactone and 90 g isoamyl lactate. Both samples were split in 50 ml samples and stored at 4 and at 40° C. respectively. After 2 months of storage they were analyzed with HPLC-ELSD. The results are as illustrated by the chromatograms depicted in FIG. 5 and FIG. 6. After 2 months of storage at either 4° C. (FIG. 5) or 40° C. (FIG. 6) of this non-aqueous sophorolactone solution only a negligible hydrolysis of lactone material occurred as evidenced by an acid sophorolipid peak appearing at 30.5 min in the grey overlay graph. This peak represents less than 1% of the total peak area.

What is claimed is:

1. Formulation consisting of a surfactant composition consisting of 70 wt %-99.9 wt % sophorolactone, 0-1 wt % sophorolipid acid, less than 0.1% residual substrate and water and a solvent with a polarity parameter delta P between 5 and 9.5 and a hydrogen bonding parameter delta H between 8 and 15.

2. Formulation according to claim 1, wherein the solvent is selected from the group consisting of phenoxyethanol, benzyl alcohol, phenetyl alcohol, hydrocinnamylalcohol, dimethylisosorbide, methyl salicylate, 2-3-o-isopropyliden glycerin and eugenol.

3. A method for the treatment of acne or dandruff comprising applying a formulation comprising the formulation of claim 1 to a subject in need thereof.

4. Formulation consisting of 50% to 95% of a composition consisting of 70 wt %-99.9 wt % sophorolactone, 0-1 wt % sophorolipid acid, less than 0.1% residual substrate and water; and 5% to 50% of a non-ionic surfactant.

5. A formulation for household cleaning, industrial cleaning, cosmetic, agrochemical, or biocide product or a template for nanomaterial synthesis consisting of a surfactant composition consisting of 70 wt %-99.9 wt % sophorolactone, 0-1 wt % sophorolipid acid, less than 0.1% residual substrate and water as formulation auxiliary.

6. A method for preparing a household cleaning product for laundry or dishwashing comprising adjusting the pH of the household cleaning formulation of claim 5 with a pH adjusting agent to a pH of 8.5-14.0 as measured on a 1% solution of the formulation in water.

7. The method according to claim 6, wherein the formulation is in the form of a tablet.

8. A method for seed coating, soil disinfection, slug or snail baiting comprising applying the agrochemical product of claim 5 to a substrate.

9. A method for the control of lice or mite comprising applying the biocide product of claim 5 to a subject in need thereof.

* * * * *

UNITED STATES PATENT AND TRADEMARK OFFICE
CERTIFICATE OF CORRECTION

PATENT NO. : 9,795,131 B2
APPLICATION NO. : 14/123830
DATED : October 24, 2017
INVENTOR(S) : Dirk Develter et al.

Page 1 of 2

It is certified that error appears in the above-identified patent and that said Letters Patent is hereby corrected as shown below:

In the Specification

In Column 1 at Line 35, Change "Candia" to --Candida--.

In Column 1 at Line 36, Change "batistae" to --batista--.

In Column 1 at Line 36, Change "Wickerhamilella" to --Wickerhamiella--.

In Column 3 at Line 39, Change "phenetyl" to --phenethyl--.

In Column 3 at Lines 40-41, Change "2-3-o-isopropyliden" to --2-3-o-isopropylidene--.

In Column 4 at Line 41, Change "and or" to --and/or--.

In Column 7 at Line 64, Change "phenetyl" to --phenethyl--.

In Column 8 at Lines 12-13 (approx.), Change "phenetyl" to --phenethyl--.

In Column 8 at Line 22, Change "phenetyl" to --phenethyl--.

In Column 8 at Lines 25-26, Change "2-3-o-isopropyliden" to --2-3-o-isopropylidene--.

In Column 8 at Line 28, Change "phenetyl" to --phenethyl--.

In Column 8 at Lines 30-31 (approx.), Change "2-3-o-isopropyliden" to --2-3-o-isopropylidene--.

In Column 8 at Line 37 (approx.), Change "2-3-o-isopropyliden" to --2-3-o-isopropylidene--.

In Column 8 at Line 45, Change "phenetyl" to --phenethyl--.

Signed and Sealed this
Fourteenth Day of May, 2019

Andrei Iancu
*Director of the United States Patent and Trademark Office*

CERTIFICATE OF CORRECTION (continued)
U.S. Pat. No. 9,795,131 B2

In Column 8 at Line 47, Change "2-3-o-isopropyliden" to --2-3-o-isopropylidene--.

In Column 8 at Line 52, Change "phenetyl" to --phenethyl--.

In Column 8 at Line 54, Change "2-3-o-isopropyliden" to --2-3-o-isopropylidene--.

In Column 8 at Line 66, Change "phenetyl" to --phenethyl--.

In Column 9 at Line 43, Change "Chrysanthenum" to --Chrysanthemum--.

In Columns 9-10 at Line 14 (approx., TABLE 1), Change "Phenetyl" to --Phenethyl--.

In Columns 9-10 at Line 33 (approx., TABLE 1), Change "2-3-o-isopropyliden" to --2-3-o-isopropylidene--.

In Column 11 at Line 7, Change "repellants" to --repellents--.

In Column 11 at Line 22, Change "Varoa" to --Varroa--.

In Column 11 at Line 22, Change "feromone" to --pheromone--.

In Column 11 at Line 26, Change "Varoa. 2-hepanone" to --Varroa. 2-heptanone--.

In Column 14 at Line 29, Change "dean," to --clean,--.

In Column 16 at Line 15 (approx.), Change "(ie" to --(i.e.--.

In Column 16 at Line 25, Change "methoxypoly (ethylene oxide)" to --methoxypoly(ethylene oxide)--.

In Column 25 at Line 6, Change "coamphoacetate," to --cocoamphoacetate,--.

In Column 25 at Line 32 (approx.), Change "Dehydrol" to --Dehydol--.

In Column 25 at Line 39 (approx.), Change "Dehydrol" to --Dehydol--.

In the Claims

In Column 26 at Line 65, In Claim 2, change "phenetyl" to --phenethyl--.

In Column 26 at Line 66, In Claim 2, change "2-3-o-isopropyliden" to --2-3-o-isopropylidene--.